(12) United States Patent
O'Leary et al.

(10) Patent No.: US 6,830,763 B2
(45) Date of Patent: Dec. 14, 2004

(54) CONTINUOUS ACIDIFICATION DEMINERALIZATION PROCESS FOR PRODUCING OSTEOINDUCTIVE BONE; AND OSTEOINDUCTIVE BONE PRODUCED THEREBY

(75) Inventors: Robert K. O'Leary, Deltaville, VA (US); Jan Zajdowicz, Lakewood, CO (US); Lloyd Wolfinbarger, Jr., Virginia Beach, VA (US)

(73) Assignee: LifeNet

( * ) Notice: Subject to any disclaimer, the term of this patent is extended or adjusted under 35 U.S.C. 154(b) by 0 days.

(21) Appl. No.: 10/180,989

(22) Filed: Jun. 26, 2002

(65) Prior Publication Data

US 2003/0012821 A1 Jan. 16, 2003

Related U.S. Application Data

(63) Continuation-in-part of application No. 09/655,711, filed on Sep. 5, 2000, now Pat. No. 6,534,095.
(60) Provisional application No. 60/152,272, filed on Sep. 3, 1999.

(51) Int. Cl.[7] ............................. A61K 35/32; C12N 5/00
(52) U.S. Cl. ..................... 424/549; 435/378; 435/284.1
(58) Field of Search ......................... 424/549; 435/378, 435/284.1, 286.5, 288.1

(56) References Cited

U.S. PATENT DOCUMENTS

| | | | | |
|---|---|---|---|---|
| 4,678,470 | A | * | 7/1987 | Nashef et al. |
| 6,030,635 | A | * | 2/2000 | Gertzman et al. |
| 6,189,537 | B1 | * | 2/2001 | Wolfinbarger, Jr. |
| 6,294,187 | B1 | * | 9/2001 | Boyce et al. |
| 6,305,379 | B1 | * | 10/2001 | Wolfinbarger, Jr. |

OTHER PUBLICATIONS

Lewandrowski et al. 1996. J. Biomed. Mat. Res. vol. 31, pp. 365–372.*

Reddi et al. 1972. Proc. Nat. Acad. Sci. USA. vol. 69, No. 6, pp. 1601–1605.*

* cited by examiner

*Primary Examiner*—Christopher R. Tate
(74) *Attorney, Agent, or Firm*—Hale and Dorr LLP

(57) ABSTRACT

The invention is directed to a process for producing demineralized osteoinductive bone, and demineralized osteoinductive bone produced thereby. The process achieves demineralization of bone by subjecting bone, including for example ground bone, bone cubes, chips, strips, or essentially intact bone, to a rapid continuous acid demineralization process. The process includes subjecting bone to a continuous exchange of demineralizing acid solution where the demineralizing acid solution is recirculated from the substantially closed container through an ion exchange media to remove calcium and phosphate thereby producing a regenerated acid, and returning the regenerated acid to the substantially closed container to produce osteoinductive demineralized bone. The process allows bone to be rapidly demineralized to a precise and specific desired residual calcium level, without sacrificing osteoinductivity.

36 Claims, 2 Drawing Sheets

CONTINUOUS ACIDIFICATION DEMINERALIZATION PROCESS FOR PRODUCING OSTEOINDUCTIVE BONE; AND OSTEOINDUCTIVE BONE PRODUCED THEREBY

RELATED APPLICATIONS

This Application is a Continuation-In-Part of application No. 09/655,711, filed Sep. 5, 2000, now U.S. Pat. No. 6,534,095, which claims the benefit of Provisional Application No. 60/152,272, filed Sep. 3, 1999.

FIELD OF THE INVENTION

The invention is a process for producing demineralized osteoinductive bone, and demineralized osteoinductive bone produced thereby. The process achieves demineralization of bone by subjecting bone, including for example ground bone, bone cubes or strips, and essentially intact bone, to a continuous exchange of acid. The process allows bone to be rapidly demineralized to a precise and specific desired residual calcium level, without sacrificing osteoinductivity.

BACKGROUND OF THE INVENTION

Demineralized freeze-dried bone allograft is widely used in the repair of skeletal defects and periodontal disease. It is known that the implantation of acid demineralized bone in the form of a powder in extraskeletal sites may stimulate new bone formation. Various groups including Syftestad, 1982; Urist et al., 1967; Urist and Strates, 1979; Urist and Strates, 1971; Urist et al., 1983; have suggested that a noncollagenous protein or proteins present in demineralized bone has the ability to induce new bone formation when present within the implanted bone matrix.

Current procedures used to demineralize ground bone involve the use of ethanol to remove lipids and hydrochloric acid to remove the mineral components of bone. These known methods are problematic in that they require prohibitively long periods of time for processing resulting in a very low demineralization rate; require excessive handling of the ground bone being processed; are capable of processing only small amounts of ground bone; and result in a demineralized bone product which exhibits inferior osteoinductivitiy caused by excessive exposure of bone inducing proteins in the bone to harsh acids over extended periods of time.

SUMMARY OF THE INVENTION

The invention achieves high demineralization rates by subjecting bone, for example ground cortical bone, to rapid and continuous exchanges of acid. Suitable acids include both highly ionized and/or weak acids. The inventors have discovered that the acid neutralization rate of bone mineral apatite is highly dependent upon the bone surface concentration of the acid and the demineralization reaction products. The initial reaction rate of the acid at the surface of the bone particle is very rapid and quickly terminates, due to boundary layer resistance caused by the increasing concentrations of the reaction by-products, if the residual reaction products are not promptly removed. Since the bone is subjected to the demineralizing acid for very brief periods of time, bone-inducing proteins are not adversely affected, thus resulting in a bone product, which achieves maximum potential osteoinductivity. The process also allows the demineralization of an entire single donor's tissue volume in a single batch.

The invention provides a rapid demineralization process for producing osteoinductive bone, including subjecting bone to continuous exchange of acid to produce demineralized bone.

The invention also provides a rapid demineralization process for producing osteoinductive bone, including subjecting bone to a continuous exchange of a predetermined volume of one or more demineralizing acid solutions under conditions effective to produce demineralized bone.

The invention further provides a rapid demineralization process where acid is continuously exchanged by recirculating a volume demineralizing acid solution from the reaction chamber containing bone to be demineralized, through an ion exchange media to remove calcium thereby producing regenerated acid, and returning the regenerated acid to the reaction chamber, where recirculation is carried out for an interval of time corresponding to a desired residual calcium level.

The invention also provides a rapid demineralization process for producing osteoinductive demineralized bone, including placing an amount of bone to be demineralized into a substantially closed container, and subjecting the bone to a continuous exchange of a demineralizing acid solution to produce osteoinductive demineralized bone.

The invention provides a rapid demineralization process where the step of subjecting includes agitation including for example, stirring, shaking, orbital shaking, and/or sonicating.

The invention further provides a rapid demineralization process where the ion exchange media is agitated during processing for example by stirring, shaking, orbital shaking, and/or sonicating.

The invention provides a rapid demineralization process for demineralizing bone by subjecting bone to a continuous exchange of a demineralizing acid solution, under conditions sufficient to achieve a demineralization rate of from about 1.5 g demineralized bone per minute to about 30.0 g per minute, preferably form about 5.0 g per minute to about 30.0 g per minute, more preferably from about 8.0 g per minute to about 25.0 g per minute, even more preferably from about 10.0 g demineralized bone per minute to about 22.0 g per minute, most preferably about 20.0 g demineralized bone per minute.

The invention further provides a rapid demineralization process for demineralizing bone (preferably to about 2.0 wt % residual calcium) where the continuous exchange of acid is carried out over intervals of from about 1.0 minutes to about 30 minutes, preferably from about 2.0 minutes to about 25.0 minutes, and more preferably from about 3.0 minutes to about 20.0 minutes, and most preferably about 4.0 minutes to about 11.0 minutes to achieve about 2.0 wt % residual calcium.

The invention also provides a rapid demineralization process for demineralizing bone by subjecting bone to a continuous exchange of acid, where the bone is demineralized until a specific desired residual calcium level is achieved.

The invention provides a rapid demineralization process for demineralizing bone where calcium is continuously removed from the demineralizing acid solution.

The invention provides a rapid demineralization process for demineralizing bone where calcium and phosphate are continuously removed from the demineralizing acid solution.

BRIEF DESCRIPTION OF THE FIGURES

The invention is further explained in the description which follows with reference to the figures and drawings, by way of non-limiting examples, various embodiments of the invention, with like reference legends representing similarly collected data throughout the sever figures and drawings.

FIG. 1 illustrates an embodiment of the apparatus and process for demineralizing bone according to the inventive process.

FIG. 2 illustrates a preferred embodiment of the inventive apparatus and process for demineralizing bone according to the inventive process.

DESCRIPTION OF THE PREFERRED EMBODIMENTS

Figure 1:
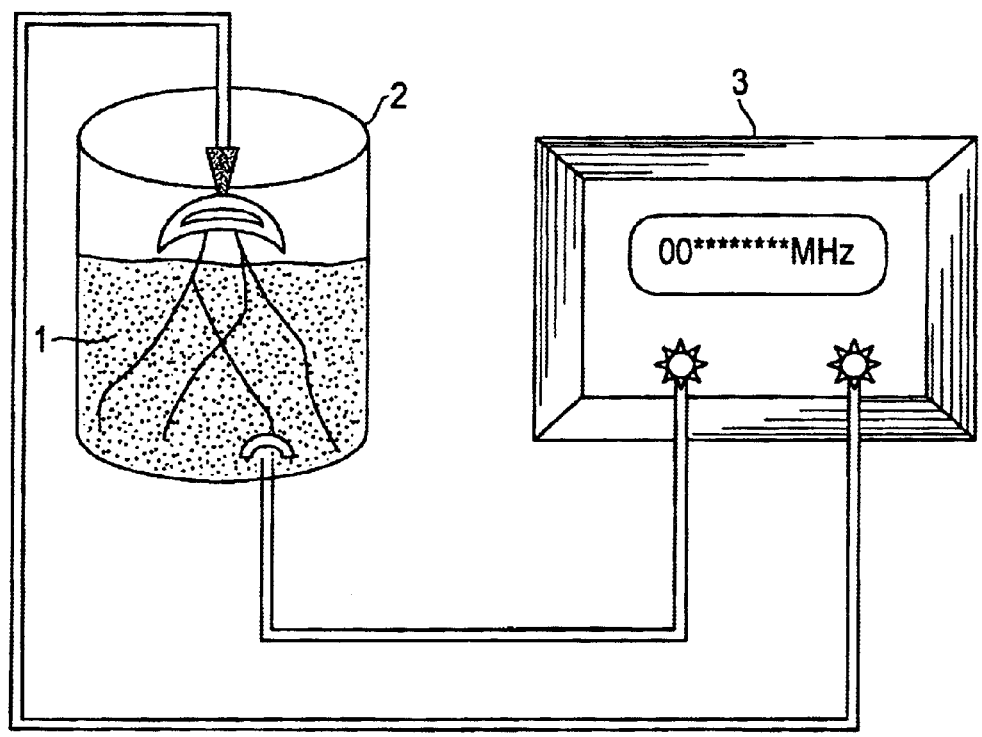
FIG. 1.

I. Definitions: The below definitions serve to provide a clear and consistent understanding of the specification and claims, including the scope to be given such terms.

Acid. By the term "acid" is intended any acid or acid solutions containing one or more acids, capable of demineralizing bone including for example, highly ionizable acids including but not limited to hydrochloric acid; and weakly ionizable acids including but not limited to citric acid. Such acid solutions may also include solutions of one or more acids in one or more alcohols, such alcohols including for example ethanol, and IPA, and solutions of one or more acids in glycerol or other organic and/or inorganic metal remover, i.e. metal chelator. Suitable acids include but are not limited to: formic acid, acetic acid, citric acid, propionic acid (organic acid), hydrochloric acid, phosphoric acid (inorganic acid); physiological tissue compatible hydroxy carboxylic acids including for example but not limited to: citric acid, gluconic acid, malic acid, tartaric acid, fumaric acid, and phosphoric acid; combinations which chelate calcium; and/or amino carboxylic agents including chelators including for example ethylenedediaminetetracetic acid (EDTA) (or analogues of this chelator), NTA, citric acid, succinic acid, and heparin can be used to chelate (bind) calcium which aids in the demineralization of bone by both organic and inorganic acids. Hydroxy carboxylic acids alone or in combination with amino carboxylic agents are advantageous for use in the demineralization process because they reduce the hydrolytic attack on bone morphogenic proteins present in the bone and because they are antioxidants which antioxidants serve as preservatives of the bone, thus eliminating the need for freeze drying the bone to preserve it.

Allowash™ Solution. By the term "Allowash™ solution" is intended for the purposes of this invention those detergent compositions disclosed in U.S. Pat. No. 5,977,034, incorporated herein by reference. Examples of suitable Allowash™ compositions include: a cleaning composition containing about 0.06 wt % polyoxyethylene-4-lauryl ether; about 0.02 wt % poly (ethylene glycol)-p-nonyl-phenyl-ether; about 0.02 wt % octylphenol-ethyleneoxide and endotoxin free deionized/distilled water.

Bone. By the term "bone" is intended for the purposes of the invention, autograft bone, allograft bone and xenograft bone. Such bone includes any bone from any source, including for example, human bone for example from: a living donor, or a cadaveric donor, and animal bone. The bone may include cortical bone and/or cancellous bone and/or cortico cancellous bone, in any form including for example, ground bone, particulate bone (i.e. dental bone) preferably in the particle size range of from about $120\mu$ to about $860\,\mu$, bone chips, bone strips, bone cubes, and essentially intact bone.

Bone Marrow Elements. By the term "bone marrow elements" is intended the highly cellular hematopoietic connective tissue filling the medullary cavities and spongy epiphyses of bones which may harbor bacterial and/or viral particles and/or fungal particles, and includes, for example blood and lipid.

Cycle. By the term "cycle" is intended one complete rotation of the tray of an orbital shaker, including for example orbital shaker by Troemner, Inc., model 980001, Serial No: 1035; 500 watts, this orbital shaker is preferably operated at a setting of from about 150 to about 210, more preferably from about 160 to about 170, which settings correlate to about from 20 to about 60 cycles/min.

Detergent. By the term "detergent" is intended any agent which through a surface action that depends on it possessing both hydrophilic and hydrophobic properties and/or exerts oil-dissolving (cleansing) and/or antibacterial and/or antiviral effects, and can include but is not limited to: anionic detergents, cationic detergents, acridine derivatives, long-chain aliphatic bases or acids, and Allowash™ detergent solutions.

Disinfectant. By the term "disinfectant" is intended one or more decontaminating agents which remove or inactivate/destroy and infectious material potentially present in the bone marrow of a bone graft; including for example, bacteria, virus and/or fungi; with such decontaminating agents including for example, an antibacterial agent; an antiviral agent; an antimycotic agent; an alcohol including for example, methyl, ethyl, propyl, isopropyl, butyl, an/or t-butyl; trisodium phosphate; sodium hydroxide; hydrogen peroxide; and/or and detergent.

Lipid. By the term "lipid" is intended the fat-soluble constituents of bone marrow, including for example fatty acids, glycerides, and phospholipids.

Solvent. By the term "solvent" is intended for the purposes of the invention, a liquid cleaning composition capable of: facilitating the solubilization of lipid, facilitating bone marrow removal, inactivating viral and/or bacterial particles, and/or disrupting cell membranes, and/or demineralizing bone, which may contain, but is not limited to, one or more of the following: water; saline; a detergent; a disinfectant; an acid; an alcohol, for example, ethanol and/or isopropanol; solvents; a combination of solutes desired to facilitate solubilization of bone marrow, including for example Allowash™ detergent solutions; a chelating agent; a bactericidal agent; an antimycotic agent; sodium hydroxide or similar strong base; organic and/or inorganic acid known and used in the art for the demineralization of bone including for example hydrochloric acid; and/or hydrogen peroxide. Known lipophilic solvents include for example, ethanol and chloroform.

Substantially Closed Processing Container. By the term "substantially closed processing container" is intended for the purposes of the present invention, any rigid or deformable container or reservoir of a size sufficient to contain bone and a predetermined volume of one or more demineralizing acids, composed of a material that is stable when in contact with the demineralizing acids, and is configured to allow the continuous exchange of acid.

Undesirable Constituents. By the term "undesirable constituents" is intended for the purposes of the present invention any constituents normally associated with a particular tissue whose presence in that tissue to be transplanted is undesirable, for example, blood cells; bacteria; fungi; viruses; in the case of bone, bone marrow elements including lipid and blood, and any other constituents normally associated with bone marrow as well as any bacterial, viral or fungal contamination associated with the bone and/or bone marrow elements.

Ion Exchange Media. By the term "ion exchange media" is intended any media capable of removing calcium and/or from a demineralizing acid solution, including for example 8% crosslinked DOWEX 50WX8 50–100 mesh which is a cation exchange resin. Anion and cation resins are available with mesh sizes including 50-100, 100–200, and 200–400. There are three resin types, strong acid cation exchange resins designated as 50W, Type I strong base anion exchange resins designated as 1, and Type II strong base anion resins designated as 2. DOWEX resins are fine mesh resins produced by Dow Chemical Co., Midlant Mich., and is a microporous copolymer of styrene and divinylbenzene (DVB). Cross-linkage is measured by percent DVB content, and includes 2, 4, and 8. This enables selection of optimum levels of permeability, water retention capacity, and total capacity. Suitable ion exchange medias include mixtures of cation and anion resins and include for example one-third DOWEX 50WX8 50–100 mesh, one-third DOWEX 1 50–100 mesh, and one-third DOWEX 2 50–100 mesh; one-half DOWEX 1 50–100 mesh, Cl form and one-half DOWEX 50WX8 50–100 mesh, H form; and 200–400 mesh at 1 liter per minute.

The inventive process allows for the decalcification of an entire single donor's tissue volume in a single vessel over a tissue weight range of 100 to 800 grams or more, at a rapid demineralization rate, over a short period of time. The bone produced is uniformly demineralized and optimally osteoinductive.

II. Procurement and Processing of Bone:

Bone is procured and processed according to methods well known in the art to which the invention pertains. For example, bone is procured from a cadaver donor, cleaned of soft tissue, and bone marrow elements and undesirable constituents are removed. The bone is then processed to a desired form including for example, ground into particulate bone, cut into cubes or strips, or left essentially intact. Bone is procured and processed under conditions according to accepted industry standards. Both cortical and/or cancellous bone is suitable for use in the inventive process.

III. Demineralization of Bone:

Using the inventive process, bone is demineralized with acid, including for example relatively strong acids such as hydrochloric acid at concentration sufficient to demineralize bone, for example from about 0.1N to about 3.0N and relatively weak acids including for example, citric acid at concentrations sufficient to demineralize bone, for example of from about 0.5N to about 5.0N. The acid, for example, citric acid, may be dissolved in one or more lipid soluble alcohols containing permeation enhancement surfactants to enhance the chemical reactivity and physical penetration of the acid into the mineral apatite of the bone. Weak acids including citric acid may be used in combination with low concentrations of strong acids including for example hydrochloric acid, to provide a demineralization system in which a desired pH, for example a pH of 1.2 which pH has been found to correlate to a residual calcium level of about 2.0 wt %, could not be exceeded, thus eliminating the potential of over decalcifying the bone matrix.

The rate of demineralization, i.e. grams of bone demineralized per minute, can be increased or decreased as desired, by one of ordinary skill in the art to which the present invention pertains and without undue experimentation, based on factors which include: the reaction temperature; the concentration or normality of the acid and the acid's neutralization potential (strong or weak) in reacting with Ca++ hydroxy apatite; the acid's dissociation or percent ionization; the delivery rate of the acid to the bone or the bone to the acid; the mass, volume and density of the bone to be demineralized; the concentration of the calcium hydroxyapatite in the bone; the degree to which the bone has been cleaned of fat and protein; the surface area of the bone particles and their particle size distribution; the compaction of the bone upon contact with the acid by the action of the acid on the bone and the rate at which the products (calcium and phosphate) are removed from the acid; the method of agitation, i.e. mechanical stirring; shaking; orbital shaking; sonication; as well as other methods of agitation which provide uniform concentration of the reacting species and reduction of boundary layer resistance; and the degree to which a boundary layer resistance forms on the microporous surface of the bone particle and the packing of these particles with each other. Accordingly, the demineralization rate can be increased for example, by increasing any one or more of the foregoing factors, for example, by increasing the temperature, acid concentration; surface area of the bone to be demineralized; and increasing agitation. Likewise, the demineralization rate can be decreased by decreasing any one or more of the foregoing factors, for example, decreasing the acid concentration, slowing the delivery of acid, and/or increasing bone particle size.

The process includes continually pumping the demineralizing acid solution through an ion exchange column which removes both the cations (calcium) and anions (phosphate), to continuously remove calcium while regenerating the acid. Suitable ion exchange media includes an 8% crosslinked DOWEX 50WX8 50–100 mesh which will remove calcium ions from dilute acid. The acid competes with the calcium for the binding sites. The lower the concentration of acid, the greater the efficacy of calcium removal. Phosphate anion removal requires an anion exchange resin including for example DOWEX 1 and DOWEX 2. These ion exchange medias will maintain the pH of the bone-acid reaction mixture thus eliminating the necessity of stopping the demineralization process in order to remove the solubilized calcium from the bone tissue. The ion exchange columns can be inactivated, for example, by a flow valve when it is time to wash the demineralized bone at the end of the demineralization process. The ion exchange columns can be reused, resterilized and through the use of "selectivity charts" can be optimized for efficacy.

(A) Determining a Desired Residual Calcium Level

The rapid demineralization inventive process is stopped when a desired residual calcium level of calcium in the bone matrix being demineralized has been reached. U.S. Pat. Nos. 6,189,537 and 6,305,379, are directed to methods for producing osteoinductive bone, and osteoinductive bone produced, and are hereby incorporated herein by reference in its entirety. To determine a stopping point, a particular pH of eluent acid (exiting the reaction chamber prior to being run through an ion exchange media, during recirculation) which correlates with the desired residual calcium level, must be determined. This is done by first obtaining a bone sample and determining the initial calcium concentration of the bone according to methods well known in the art to which the invention applies; demineralizing bone at a constant rate; simultaneous with demineralizing, periodically sampling the eluent acid solution and the bone from the closed reaction container at specific intervals of time during the demineralization process; determining the pH of each sample of acid solution and determining the residual calcium level of each corresponding bone sample; plotting the pH of a sample versus the calcium concentration of the corresponding bone sample, and drawing a curve; and from the curve determining what pH of the acid correlates with the desired residual calcium level. Thereafter, the residual calcium level of a bone sample can be determined by determining the pH of a sample of the acid solution, sampled at a time point during demineralization of the bone sample, by determining the calcium concentration on the curve which corresponds to the pH of the acid sample.

(B) Determining the Amount of Acid:

A preferred method for determining the amount of acid needed is as follows: The weight of the ground bone is first determined. Thereafter, the donor weight in grams is divided by 100 grams and the resultant number is multiplied by 1 liter. The resultant number is the total volume of acid needed to demineralize the given amount of ground bone. Generally, about four liters of acid is sufficient for an amount of ground bone from a single donor (100 to 800 grams of ground bone).

Other acids and desired calcium levels can be used, by monitoring the calcium levels during demineralization at specific time points and plotting a curve to determine how much acid is used to reach a specific calcium level.

IV. FIG. 1.

FIG. 1 illustrates the apparatus of the invention. Bone is demineralized by placing bone, for example ground bone, in reaction vessel 1 containing a demineralization solution, for example one or more acids at a concentration sufficient to demineralize bone, and in a volume sufficient to process the amount of bone to be demineralized, for example from about 2.0 to about 108.0 liters, preferably from about 3.0 to about 7.0 liters of acid. Thereafter, a defoaming agent is added to the vessel through inflow tubing 5 connected to inlet 4. Suitable defoamers include any defoamers well known in the art to which the invention pertains, and include for example ethanol, for example 60 mls of 200 proof ethanol in 6.0 liters of acid. The bone-acid-ethanol solution is then preferably vigorously agitated, such agitation including for example stirring at from about 500 rpm to about 2500 rpm, preferably 1000 rpm to about 2000 rpm, and more preferably stirred at about 1350 rpm with mixing paddle 6, for example Cole Palmer Model No: E-04541-00 303/304 supplied by Cole Palmer Instrument Co., Vernon Hills, Ill.; or orbital shaking; while the system is maintained at a desired temperature, for example of from about 0° C. to about 100° C., preferably from about 15° C. to about 50° C., more preferably from about 20° C. to about 40° C., and most preferably at about 23° C. The demineralizing acid solution is continuously exchanged by pumping the acid solution from the reaction vessel 1, through outlet 2, through outflow tubing 3, which tubing runs through pump 6, pump 6 is operated at from 0.25 to 4.0 liters per min., preferably 0.5 to 2.0 liters per min, and most preferably about 1.0 liter per min., and the eluent acid solution is delivered to ion exchange media vessel 7 through inlet 8. The acid solution is continually pumped and calcium and phosphate are removed from the acid solution by the ion exchange media 10, the regenerated acid exits the ion exchange media at outlet 9, and flows back into the reaction vessel 1 through inflow tubing 5. The ion exchange media vessel 7 is disposed on a magnetic stir plate 11 to stir the ion exchange media 10 during the process. The reaction vessel 1 is disposed on an orbital shaker 12 to agitate the acid/bone mixture during processing.

FIG. 2.

Figure 2:
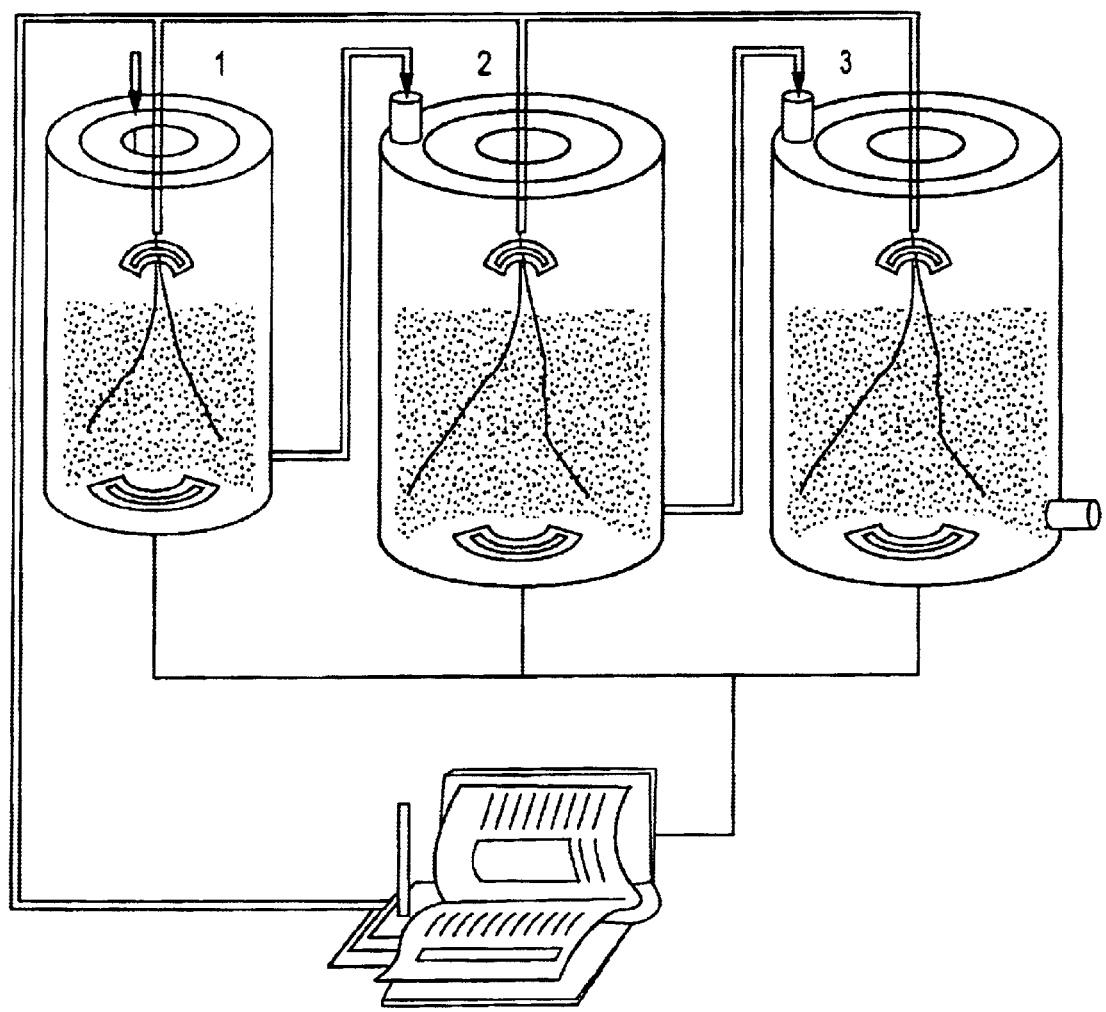
FIG. 2.

FIG. 2 illustrates a preferred embodiment of the apparatus of the invention. Bone is demineralized by placing bone, for example ground bone, in reaction vessel 1 containing a demineralization solution, for example one or more acids at a concentration sufficient to demineralize bone, and in a volume sufficient to process the amount of bone to be demineralized, for example from about 2.0 to about 10.0 liters, preferably from about 3.0 to about 6.0 liters of acid. Thereafter, a defoaming agent is added to the vessel through inflow tubing 5. Suitable defoamers include any defoamers well known in the art to which the invention pertains, and include for example ethanol, for example 60 mls of 200 proof ethanol in 6.0 liters of acid. The bone-acid-ethanol solution is then preferably vigorously agitated, such agitation including for example stirring at from about 500 rpm to about 2500 rpm, preferably 1000 rpm to about 2000 rpm, and more preferably stirred at about 1350 rpm with mixing paddle 6, for example Cole Palmer Model No: E-04541-00 303/304 supplied by Cole Palmer Instrument Co., Vernon Hills, Ill.; or orbital shaking; while the system is maintained at a desired temperature, for example of from about 0° C. to about 100° C., preferably from about 15° C. to about 50° C., more preferably from about 20° C. to about 40° C., and most preferably at about 23° C. The demineralizing acid solution is continuously exchanged by pumping the acid solution from the reaction vessel 1, through outflow tubing 3, which tubing runs through pump 6, pump 6 is operated at from 0.25 to 4.0 liters per min., preferably 0.5 to 2.0 liters per min, and most preferably about 1.0 liter per min., and the eluent acid solution is delivered to in-line ion exchange media vessel 7 through inlet 8. The acid solution is continually pumped and calcium and phosphate are removed from the acid solution by the ion exchange media 10, the regenerated acid exits the ion exchange media at outlet 9, and flows back into the reaction vessel 1 through inflow tubing 5. The reaction vessel 1 is disposed on an orbital shaker 12 to agitate the acid/bone mixture during processing.

All of the publications cited herein are hereby incorporated by reference into the present disclosure. It will be appreciated by those skilled in the art to which the invention pertains that various modifications can be made without departing from the essential nature thereof. It is intended to encompass all such modification within the scope of the appended claims.

We claim:

1. A rapid demineralization process for producing osteoinductive bone, comprising subjecting bone to a continuous exchange of a predetermined volume of a demineralizing acid solution to produce demineralized bone, wherein said volume of demineralizing acid solution is recirculated from a substantially closed container containing bone to be demineralized through an ion exchange media to remove calcium and phosphate thereby producing a regenerated acid, and said regenerated acid is returned to said substantially closed container.

2. A rapid demineralization process for producing osteoinductive bone, comprising subjecting bone to a continuous exchange of a predetermined volume of a demineralizing acid solution under conditions effective to produce demineralized bone wherein said volume of demineralizing acid solution is recirculated from a substantially closed container containing bone to be demineralized through an ion exchange media to remove calcium and phosphate thereby producing a regenerated acid, and said regenerated acid is returned to said substantially closed container.

3. A rapid demineralization process for producing osteoinductive demineralized bone, comprising placing an amount of bone to be demineralized into a substantially closed container and recirculating a predetermined volume of demineralizing acid solution from said substantially closed container through an ion exchange media to remove calcium and phosphate thereby producing a regenerated acid, and returning said regenerated acid to said substantially closed container to produce said osteoinductive demineralized bone.

4. The rapid demineralization process of claim 3, where recirculation is carried out for an interval of time corresponding to a desired residual calcium level.

5. The rapid demineralization process of claim 3, further comprising agitating the substantially closed container.

6. The rapid demineralization process of claim 3, wherein said ion exchange media comprises a strong cation exchange resin.

7. The rapid demineralization process of claim 3, wherein said ion exchange media comprises a strong anion exchange resin.

8. The rapid demineralization process of claim 3, wherein said ion exchange media comprises a strong anion exchange resin and a strong cation exchange resin.

9. The rapid demineralization process of any one of claims 1, 2 or 3, wherein said bone is demineralized at a rate of from about 1.5 g/min. to about 30.0 g/min.

10. The rapid demineralization process of claim 9, wherein said bone is demineralized at a rate of greater than 10.0 g/min.

11. The rapid demineralization process of claim 10, wherein said bone is demineralized at a rate of greater than 15.0 g/min.

12. The rapid demineralization process of claim 11, wherein said bone is demineralized at a rate of greater than 20.0 g/min.

13. The rapid demineralization process of any one of claims 1, 2 or 3, said process being carried out at a temperature of from about 0° C. to about 100° C.

14. The rapid demineralization process of claim 13, said process being carried out at a temperature of from about 15° C. to about 50° C.

15. The rapid demineralization process of claim 13, said process being carried out at a temperature of from about 20° C. to about 40° C.

16. The rapid demineralization process of any one of claims 1, 2 or 3, wherein said predetermined volume comprises 10.0 liters or less.

17. The rapid demineralization process of claim 16, wherein said predetermined volume comprises 8.0 liters or less.

18. The rapid demineralization process of claim 16, wherein said predetermined volume comprises 6.0 liters or less.

19. The rapid demineralization process of claim 16, wherein said predetermined volume comprises 4.0 liters or less.

20. The rapid demineralization process of any one of claims 1, 2 or, 3, further comprising stopping said demineralization process once a predetermined residual calcium level present in said bone is achieved.

21. The rapid demineralization process of any one of claims 1 or 2, further comprising agitating the substantially closed container.

22. The rapid demineralization process of claim 21, wherein said agitation comprises stirring.

23. The rapid demineralization process of claim 22, wherein said stirring comprises stirring at from about 1000 rpm to about 2000 rpm.

24. The rapid demineralization process of claim 22, wherein said stirring comprises stirring at from about 1200 rpm to about 1500 rpm.

25. The rapid demineralization process of claim 21, wherein said agitation comprises shaking.

26. The rapid demineralization process of claim 25, wherein said shaking comprises shaking on an orbital shaker.

27. The rapid demineralization process of claim 26, wherein said orbital shaking comprises orbital shaking at a rate of from about 20 cycles/min. to about 60 cycles/min.

28. The rapid demineralization process of claim 26, wherein said orbital shaking comprises orbital shaking at a rate of from about 30 cycles/min. to about 50 cycles/min.

29. The rapid demineralization of any one of claims 1 or 2, where calcium and phosphate are continually removed from said demineralizing acid solution.

30. A rapid demineralization process for demineralizing bone, comprising subjecting bone to a continuous exchange of a demineralized acid solution, wherein said volume of demineralizing acid solution is recirculated from a substantially closed container containing bone to be demineralized through an ion exchange media to remove calcium and phosphate thereby producing a regenerated acid, and said regenerated acid is returned to said substantially closed container, wherein said bone is demineralized until a predetermined residual calcium level in said bone is achieved.

31. A rapid demineralization process for producing osteoinductive bone, comprising subjecting bone to a continuous exchange of a predetermined volume of a demineralizing acid solution to produce demineralized bone, wherein said volume of demineralizing acid solution is recirculated from a substantially closed container containing bone to be demineralized through an ion exchange media to remove calcium and phosphate thereby producing a regenerated acid, and said regenerated acid is returned to said substantially closed container, wherein calcium and phosphate are continually removed from said demineralizing acid solution.

32. A rapid demineralization process for producing osteoinductive bone, comprising subjecting bone to a continuous exchange of a predetermined volume of a demineralizing acid solution under conditions effective to produce demineralized bone, wherein said volume of demineralizing acid solution is recirculated from a substantially closed container containing bone to be demineralized through an ion exchange media to remove calcium and phosphate thereby producing a regenerated acid, and said regenerated acid is returned to said substantially closed container, wherein calcium and phosphate are continually removed from said demineralizing acid solution.

33. A rapid demineralization process for producing osteoinductive bone, comprising subjecting bone to a continuous exchange of a predetermined volume of a demineralizing acid solution maintained at a constant concentration, wherein said said volume of demineralizing acid solution is recirculated from a substantially closed container containing bone to be demineralized through an ion exchange media to remove calcium and phosphate thereby producing a regenerated acid, and said regenerated acid is returned to said substantially closed container, to produce demineralized bone.

34. The rapid demineralization process of claim 33, wherein said demineralizing acid solution is maintained at a constant concentration by recirculating said demineralizing acid solution through an ion exchange media to remove calcium and phosphate thereby producing a regenerated acid having a constant concentration.

35. The rapid demineralization process of any one of claims 33 or 34 wherein the pH of said demineralizing acid solution is maintained.

36. The rapid demineralization process of claim 35, wherein the pH is maintained within one pH unit.

* * * * *